(12) United States Patent
Füglister

(10) Patent No.: US 10,531,979 B2
(45) Date of Patent: Jan. 14, 2020

(54) TONGUE DEFORMATION IMPLANT

(71) Applicant: Fabian Hermann Urban Füglister, Würenlos (CH)

(72) Inventor: Fabian Hermann Urban Füglister, Würenlos (CH)

(*) Notice: Subject to any disclaimer, the term of this patent is extended or adjusted under 35 U.S.C. 154(b) by 581 days.

(21) Appl. No.: 14/773,629

(22) PCT Filed: Mar. 17, 2014

(86) PCT No.: PCT/IB2014/000364
§ 371 (c)(1),
(2) Date: Sep. 8, 2015

(87) PCT Pub. No.: WO2014/140777
PCT Pub. Date: Sep. 18, 2014

(65) Prior Publication Data
US 2016/0022471 A1    Jan. 28, 2016

Related U.S. Application Data

(60) Provisional application No. 61/787,006, filed on Mar. 15, 2013, provisional application No. 61/914,444, filed on Dec. 11, 2013.

(51) Int. Cl.
*A61F 5/56* (2006.01)
*A61B 17/12* (2006.01)

(52) U.S. Cl.
CPC .......... *A61F 5/566* (2013.01); *A61B 17/1214* (2013.01); *A61B 17/12022* (2013.01); *A61B 17/12145* (2013.01); *A61F 5/56* (2013.01)

(58) Field of Classification Search
CPC ...... A61F 5/56; A61F 5/566; A61F 2005/563; A61F 2/00; A61F 2/0004; A61F 2/0009;
(Continued)

(56) References Cited

U.S. PATENT DOCUMENTS 5,256,133 A * 10/1993 Spitz .................... A61B 17/064
128/DIG. 25
6,093,199 A * 7/2000 Brown ............. A61B 17/12022
606/200

(Continued)

FOREIGN PATENT DOCUMENTS

EP        1216013         6/2006
WO      2008156761       12/2008
(Continued)

OTHER PUBLICATIONS

Search Report for counterpart China Patent Application No. 201480015900.1, dated Jul. 26, 2016, PRC Patent Office, Beijing, China.

(Continued)

*Primary Examiner* — William H Matthews
(74) *Attorney, Agent, or Firm* — Babcock IP, PLLC

(57) ABSTRACT

There is provided a method and apparatus for a tongue implant to induce deformation of the tongue made of nickel titanium alloy in superelastic state at body temperature for the treatment of obstructive sleep apnea. In one embodiment the implant has a function of a V shaped spring, one leg helically inserted into the tongue, the other leg beneath the root of the tongue, to permanently compress the tongue. In another embodiment, there is provided a method and apparatus for placement of a helical implant to permanently compress the tongue by deforming it and stiffening it to maintain tongue stability for the treatment of obstructive sleep apnea.

20 Claims, 13 Drawing Sheets

(58) Field of Classification Search
CPC .... A61F 2/0022; A61F 2/0036; A61F 2/0059; A61B 17/12022; A61B 17/12036; A61B 17/1214; A61B 17/12145; A61B 17/1215
See application file for complete search history.

(56) References Cited

U.S. PATENT DOCUMENTS

| | | | |
|---|---|---|---|
| 6,221,004 B1 * | 4/2001 | Kahl | A61F 5/0093 600/29 |
| 6,453,905 B1 | 9/2002 | Conrad et al. | |
| 6,638,291 B1 * | 10/2003 | Ferrera | A61B 17/12022 606/191 |
| 8,074,654 B2 | 12/2011 | Paraschac et al. | |
| 9,089,405 B1 * | 7/2015 | Gulachenski | A61B 17/12113 |
| 9,211,210 B2 * | 12/2015 | Roue | A61F 5/56 |
| 9,675,494 B2 * | 6/2017 | Zhang | A61F 5/566 |
| 9,707,122 B2 * | 7/2017 | Gillis | A61F 5/566 |
| 2001/0037133 A1 * | 11/2001 | Knudson | A61F 2/00 607/42 |
| 2001/0050084 A1 * | 12/2001 | Knudson | A61F 2/00 128/898 |
| 2001/0050085 A1 * | 12/2001 | Knudson | A61F 2/00 128/898 |
| 2002/0010481 A1 * | 1/2002 | Jayaraman | A61B 17/0057 606/151 |
| 2003/0199974 A1 * | 10/2003 | Lee | A61F 2/2442 623/2.36 |
| 2004/0127982 A1 * | 7/2004 | Machold | A61F 2/2418 623/2.36 |
| 2004/0139975 A1 * | 7/2004 | Nelson | A61F 2/00 128/848 |
| 2004/0193246 A1 * | 9/2004 | Ferrera | A61B 17/12022 623/1.15 |
| 2005/0092332 A1 * | 5/2005 | Conrad | A61F 5/566 128/898 |
| 2005/0092334 A1 * | 5/2005 | Conrad | A61F 2/00 128/898 |
| 2005/0107823 A1 * | 5/2005 | Leone | A61B 17/12022 606/200 |
| 2005/0126563 A1 * | 6/2005 | van der Burg | A61B 17/8061 128/200.24 |
| 2005/0177228 A1 * | 8/2005 | Solem | A61F 2/2451 623/2.36 |
| 2005/0187564 A1 * | 8/2005 | Jayaraman | A61B 17/12022 606/141 |
| 2005/0187620 A1 * | 8/2005 | Pai | A61F 2/2481 623/2.37 |
| 2005/0192618 A1 * | 9/2005 | Porter | A61B 17/12022 606/200 |
| 2005/0192619 A1 * | 9/2005 | Teoh | A61B 17/12022 606/200 |
| 2005/0222661 A1 * | 10/2005 | Case | A61F 2/2475 623/1.1 |
| 2006/0015178 A1 * | 1/2006 | Moaddeb | A61F 2/2442 623/2.36 |
| 2006/0235264 A1 * | 10/2006 | Vassallo | A61B 17/24 600/37 |
| 2006/0235380 A1 * | 10/2006 | Vassallo | A61B 18/1402 606/45 |
| 2006/0241686 A1 * | 10/2006 | Ferrera | A61B 17/12022 606/200 |
| 2006/0241746 A1 * | 10/2006 | Shaoulian | A61F 2/2451 623/2.37 |
| 2007/0066863 A1 * | 3/2007 | Rafiee | A61B 17/00234 600/37 |
| 2007/0137654 A1 * | 6/2007 | Paraschac | A61F 5/56 128/848 |
| 2007/0137655 A1 * | 6/2007 | Paraschac | A61F 5/56 128/848 |
| 2007/0144531 A1 * | 6/2007 | Tomas | A61F 5/56 128/848 |
| 2007/0144532 A1 * | 6/2007 | Gillis | A61F 5/56 128/848 |
| 2007/0246052 A1 | 10/2007 | Hegde | |
| 2007/0246062 A1 | 10/2007 | Hegde et al. | |
| 2007/0261701 A1 * | 11/2007 | Sanders | A61B 17/0401 128/848 |
| 2008/0023012 A1 * | 1/2008 | Dineen | A61B 17/0401 128/848 |
| 2008/0066765 A1 | 3/2008 | Paraschac | |
| 2008/0066766 A1 * | 3/2008 | Paraschac | A61F 5/566 128/848 |
| 2008/0066767 A1 * | 3/2008 | Paraschac | A61F 5/566 128/848 |
| 2008/0066769 A1 * | 3/2008 | Dineen | A61B 17/0401 128/897 |
| 2008/0097380 A1 * | 4/2008 | Li | A61F 5/566 604/506 |
| 2008/0208265 A1 | 8/2008 | Frazier et al. | |
| 2008/0221673 A1 * | 9/2008 | Bobo | A61F 2/2451 623/2.36 |
| 2009/0038623 A1 * | 2/2009 | Farbarik | A61F 2/02 128/848 |
| 2009/0069866 A1 * | 3/2009 | Farbarik | A61B 5/0031 607/60 |
| 2009/0078257 A1 * | 3/2009 | Bhat | A61B 5/0031 128/204.23 |
| 2009/0078273 A1 * | 3/2009 | Bhat | A61B 5/0031 128/848 |
| 2009/0078274 A1 * | 3/2009 | Bhat | A61B 5/0031 128/848 |
| 2009/0078275 A1 * | 3/2009 | Hegde | A61B 5/0031 128/848 |
| 2009/0149872 A1 * | 6/2009 | Gross | A61F 2/2445 606/151 |
| 2010/0030328 A1 * | 2/2010 | Seguin | A61B 17/064 623/2.11 |
| 2010/0108077 A1 * | 5/2010 | Lindh | A61F 5/566 128/848 |
| 2010/0242967 A1 * | 9/2010 | Burbank | A61F 5/08 128/207.18 |
| 2011/0100376 A1 | 5/2011 | Rousseau | |
| 2012/0017919 A1 * | 1/2012 | Gillis | A61F 5/566 128/848 |
| 2012/0132214 A1 * | 5/2012 | Gillis | A61F 5/566 128/848 |
| 2012/0138069 A1 | 6/2012 | Gillis | |
| 2012/0192872 A1 * | 8/2012 | Rudakov | A61B 17/12036 128/831 |
| 2012/0216818 A1 | 8/2012 | Burg | |
| 2012/0312307 A1 * | 12/2012 | Paraschac | A61F 5/566 128/848 |
| 2013/0014765 A1 * | 1/2013 | Meade | A61F 5/566 128/848 |
| 2014/0000631 A1 * | 1/2014 | Gillis | A61F 5/566 128/848 |
| 2014/0007885 A1 * | 1/2014 | Gillis | A61F 5/566 128/848 |
| 2016/0022470 A1 * | 1/2016 | Gillis | A61F 5/56 128/848 |

FOREIGN PATENT DOCUMENTS

| | | |
|---|---|---|
| WO | 2012073097 | 6/2012 |
| WO | 2012075186 | 6/2012 |
| WO | 20120073097 | 6/2012 |

OTHER PUBLICATIONS

Nickoleta Kocheva, International Search Report of parent PCT Application No. PCT/IB2014/000364, dated Jun. 30, 2014, European Patent Office, Rijswijk Netherlands.

* cited by examiner

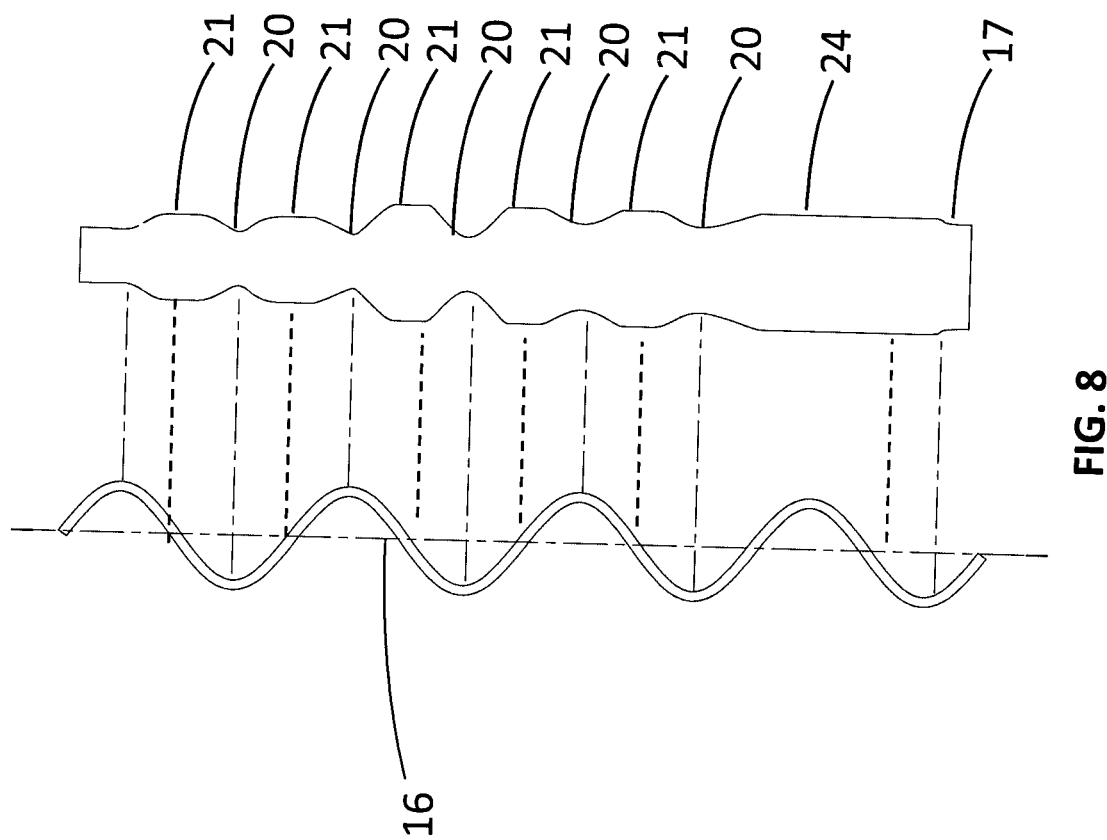

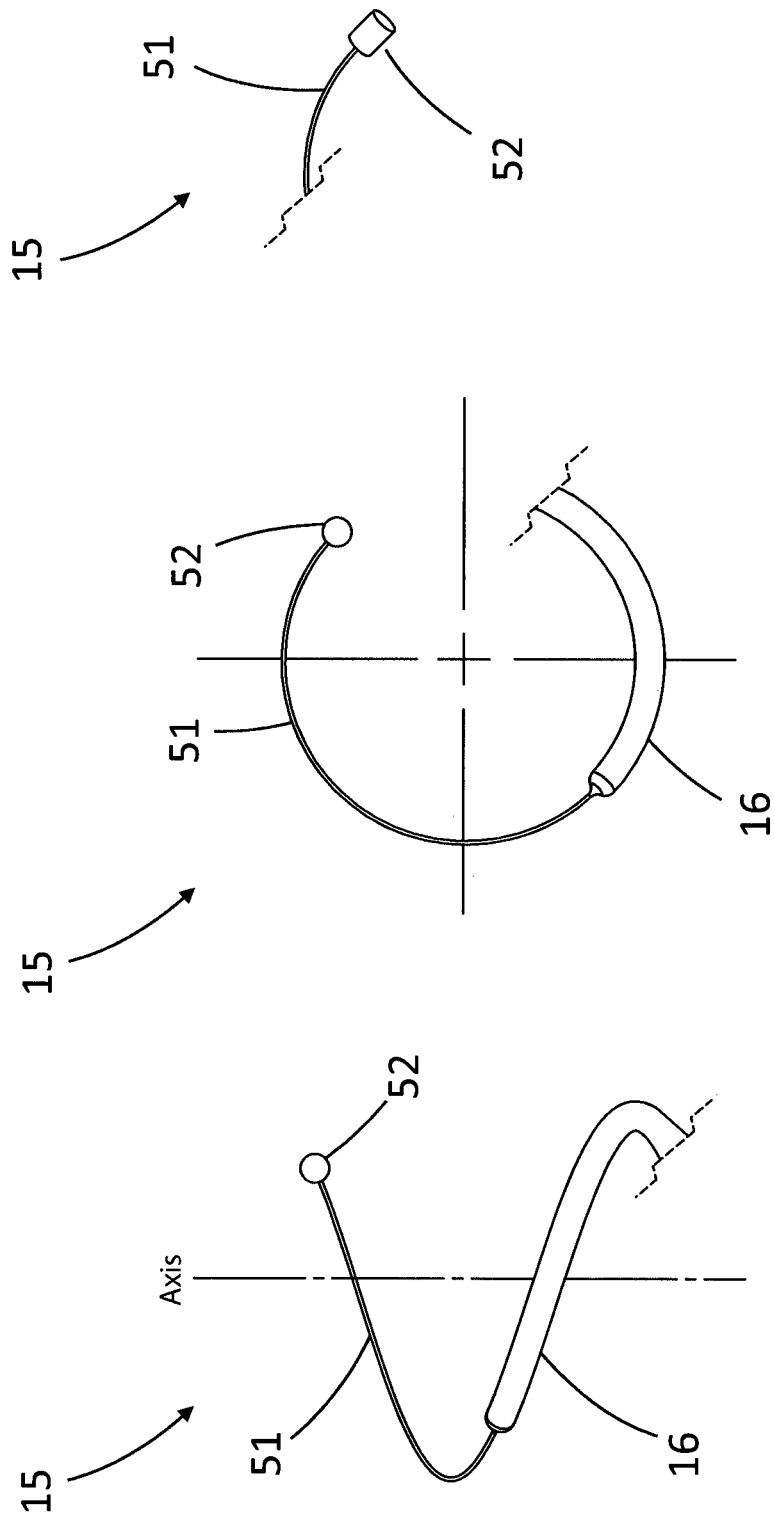

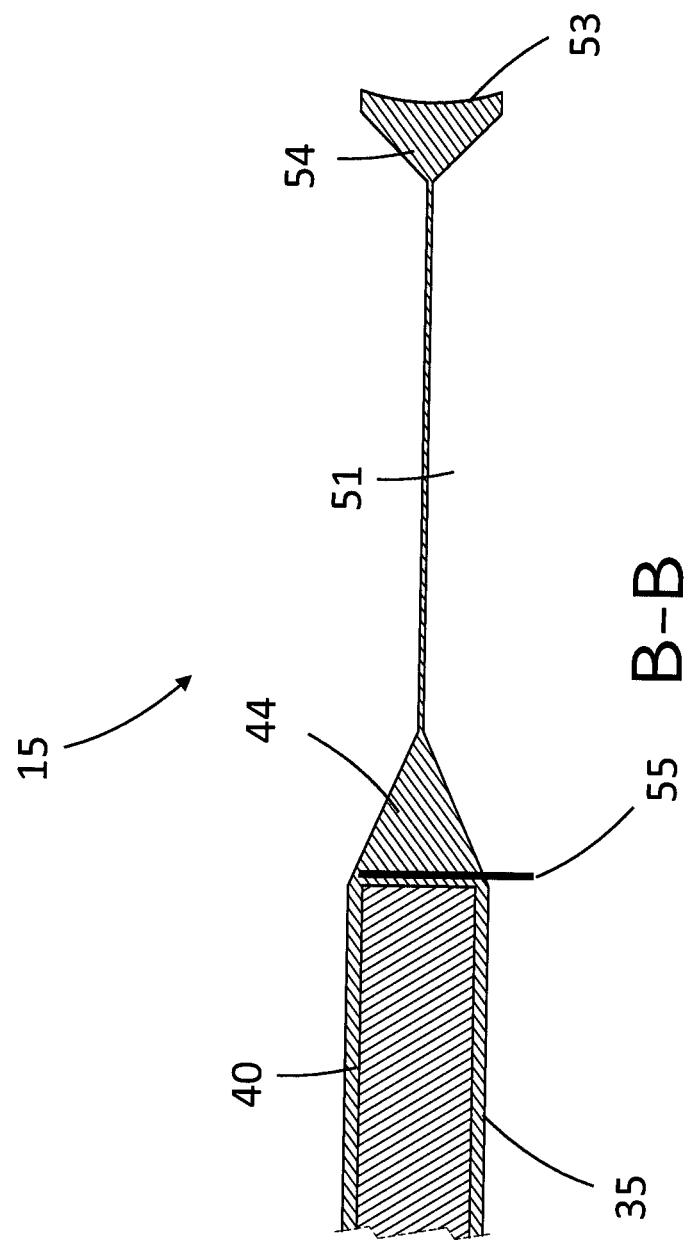

TONGUE DEFORMATION IMPLANT

CROSS REFERENCE TO RELATED APPLICATIONS

This application claims priority benefit to U.S. Provisional Application No. 61/914,444, filed 11 Dec. 2013 and U.S. Provisional Application No. 61/787,006, filed 15 Mar. 2013, and incorporates the foregoing application as well as Int. Pat. Application PCT/IB11/002878, Int. Pat. Application PCT/IB2013/001195, U.S. Provisional Application No. 61/656,582 (filed 7 Jun. 2012), by reference thereto in this application in their entirety.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

FIELD OF THE INVENTION

The present invention relates generally to the treatment of obstructive sleep apnea and snoring.

BACKGROUND OF THE INVENTION

Obstructive sleep apnea (OSA) is defined as recurrent cessation of breathing with upper airway obstruction occurring during sleep, resulting in substantially reduced (hypopnea) or complete cessation (apnea) of airflow despite ongoing breathing efforts. By convention, the patient must experience more than 30 episodes lasting more than 10 seconds or more than five abnormal breathing disturbances (hypopneas or apneas) per hour of sleep. In most cases the person is unaware that a disturbance is taking place. Referring now to FIG. 1, the human upper airway anatomy consists of the mandible bone 12, tongue 2, pharynx 3, hyoid bone 4, palate 5, uvula 6, epiglottis 7, lips 8, larynx 9, geniohyoid 10, mylohyoid 11, and adjacent facial structures. This anatomy plays a central role in speaking, breathing, mastication and swallowing. The airway is composed of numerous muscles and soft tissue but lacks rigid or bony support. Most notably, it contains a collapsible portion that extends from the hard palate 5 to the larynx 9. Although the ability of the upper airway to change shape and momentarily close is essential for speech and swallowing during an awake state, this feature also provides the opportunity for collapse at inopportune times such as during sleep. Although non-obese individuals may suffer from OSA, obesity is the main epidemiologic risk factor. It can influence both the structure and function of skeletal muscles. The interplay and correlated movements between all the anatomical structures is complex. These various physiological traits and the potential for each to influence sleep apnea pathophysiology have been described in detail in review articles. The pathophysiological causes of OSA likely vary considerably between individuals. Important components likely include upper airway anatomy, the ability of the upper airway dilator muscles to respond to respiratory challenge during sleep, the propensity to wake from increased respiratory drive during sleep (arousal threshold), the stability of the respiratory control system (loop gain), and the potential for state-related changes in lung volume to influence these factors. Ultimately, the maintenance of pharyngeal patency depends on the equilibrium between occluding and dilating forces. Upper airway dilator muscle activity is crucial to the counteraction of the negative intraluminal pressure generated in the pharynx during inspiration. Diminution of this activity during sleep is thought to play a central role in pharyngeal collapse and obstruction in patients with OSA.

The development of occlusion in this disorder has been related to "prolapsing" of the tongue into the pharynx. The tongue being prolapsed has been attributed to diminished neuromuscular activity in the genioglossus muscle inside the tongue which protrudes it forward, when it is activated. Activation of the genioglossus (GG), the main tongue protrudor, has been shown to reduce pharyngeal resistance and collapsibility by far more than all other upper airway dilators.

There are a variety of treatments for OSA, but continuous positive airway pressure (CPAP), in which a nose mask is attached via a tube to a machine to blow pressurized air into the pharynx and push the collapsed section open, is still the gold standard in treatment. Surgical procedures aiming for tissue reduction or stiffening to widen the pharynx have proven to be unreliable or to have adverse effects. However, as most patients dislike or refuse to use a mask for CPAP treatment, new procedures involving implants are needed. Multiple trials attempting to relieve OSA by functional electric stimulation of upper airway dilators during sleep resulted in modest and/or inconsistent results. Numerous attempts have been made towards treating OSA by placing implants into the tongue and are known in prior art, for example, the Pavad Medical tongue stabilization device U.S. Pat. Nos. 7,909,037 and 7,909,038, both dated Mar. 22, 2011. Another implant for treating OSA is the Restore Medical implant disclosed in U.S. Pat. No. 7,401,611 dated Jul. 22, 2008, or the Revent Medical implant disclosed in U.S. Pat. No. 8,167,787 dated May 1, 2012 and U.S. Pat. No. 8,327,854 dated Dec. 11, 2012. The contents of which is incorporated herein by reference to extent not inconsistent with the current disclosure. Another implant for treating OSA is disclosed in U.S. Pat. No. 8,220,466, the content of which is incorporated by reference hereto. This '466 patent describes a spring attached to the mandible bone, which pulls the tongue anteriorly. All of the mentioned patents involve surgical procedures, which may not be suitable for some patients and/or which are extremely time consuming for inserting or are not minimal invasive or show unsatisfying success rates.

What is needed therefore is a surgically fast and minimally invasive tongue implant to treat OSA, which can deform like the tongue to comply with physiological tasks, but changing its rigidity to reliably and safely open up the pharyngeal airway blocked by the tongue. The implant should stiffen the tongue along the base into the body of the tongue and protrude it. Furthermore, it must minimize relative movement between implanted member and surface area in contact with the tongue to avoid abrasion of the implant.

SUMMARY OF THE INVENTION

A method and apparatus for the treatment of OSA are disclosed which protrudes the tongue and hence enlarges the pharyngeal cross-sectional area by implanting a nickel titanium alloy device in superelastic state at body temperature having the function of a V shaped spring, one leg inserted helically directly from the root of the tongue near the hyoid bone, along and near the base of the tongue into the body of the tongue, the apex leaving the root of the tongue providing a torque moment, the other leg acting as a force distributor placed between the root of the tongue and the geniohyoid, or between geniohyoid and mylohyoid. Another embodiment shows placement of a helical nickel titanium alloy device in superelastic state at body temperature along and near the base of the tongue to permanently compress the tongue, hence protruding the tongue to enlarge the pharyngeal cross-sectional to prevent obstructions of the airway.

BRIEF DESCRIPTION OF THE DRAWINGS

FIG. 8 is a helical section with an exaggerated schematic view of an implant showing a profile distribution of a helical section.

FIG. 11A-C shows different views of the flexible distal end section.

FIG. 13 shows a longitudinal cross section of a different flexible distal end.

DETAILED DESCRIPTION OF THE PREFERRED EMBODIMENT

Figure 1:
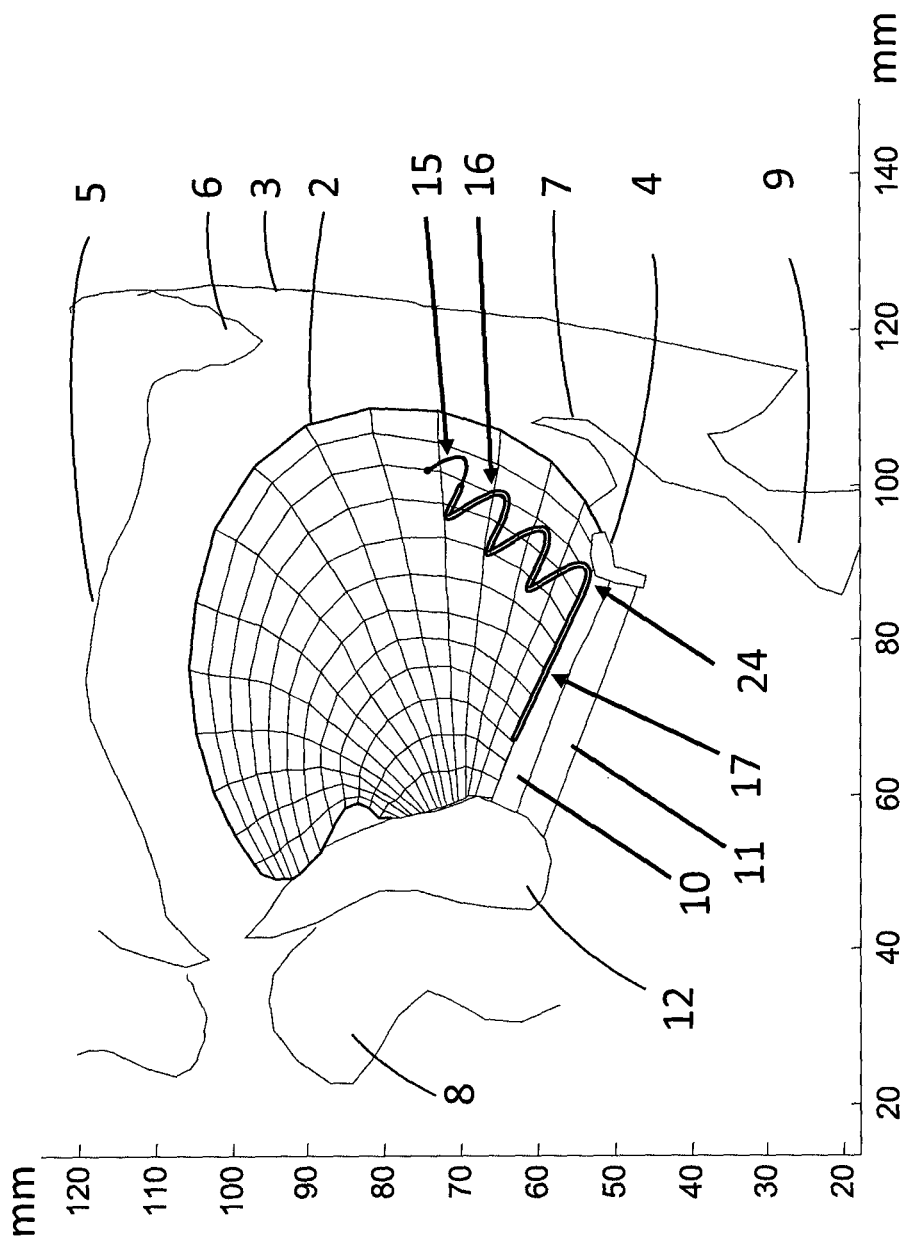
FIG. 1 is a midsagittal plane view of the pharynx with an implant helically inserted inside the tongue and the force distribution section between root of the tongue and geniohyoid muscle.

The following descriptions are of exemplary embodiments of the invention and the inventors' conception of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

The tongue is a unique and complex motor organ in the human body, but highly constrained inside the mouth. Its base is attached to the mandible and to the hyoid bone, while its upper and lateral surfaces are often in contact with the palate and the teeth. It is composed almost entirely of muscle and containing no skeleton. There are two different types of tongue muscles: intrinsic fibers, which originate and terminate within the tongue, and extrinsic fibers, those which arise externally from rigid bony surfaces. A detailed anatomical study has been described in Takemoto (2001). Activities of these muscles result in subtle movements of muscular structure and produce large deformations of the tongue's soft tissues. This is crucial for multiple physiological tasks, such as speech, mastication and swallowing. In speech, the tongue assumes stereotyped configurations which determine overall vocal tract shape, whereas in mastication and swallowing, the tongue acts to contain and propel a bolus of food. In each instance, regional activation of specific lingual muscles results in prototypical tissue deformation.

Tissue incompressibility is commonly assumed as the tissue is highly aqueous, giving the tongue its capability to behave as a muscular hydrostat, which is an organ, whose musculature creates motion and supplies skeletal support for that motion as well (like the elephant trunk or squid tentacle). This incompressibility enables quick and efficient alteration of its form while maintaining original volume. Because of the complexity of lingual anatomy and its material attributes, the relationship between tongue structure and mechanical function is difficult to understand. Owing to incompressibility and complex fiber structure, lingual mechanics cannot be readily studied from changes of overall tissue shape. It requires an analysis of the complex organization of the human tongue musculature and internal muscle dynamics to understand the occurring deformations of the tongue, which is a necessary and critical requirement in order to fully understand the scope of this invention for a permanently implanted tongue actuator or a passive tongue compressing implant to treat OSA. Biomechanical models of the tongue and vocal tract have been in use since the 1960's to study articulation. Their complexity has increased with the acquisition of new knowledge about anatomical, neurophysiological and physical characteristics of the tongue, as well as with the vast growth in the computational capacities. All these models have significantly contributed to the increase in knowledge about tongue behavior and tongue control during speech production, and more specifically about the relations between muscle recruitments and tongue shape or acoustic signal (see in particular for 2D models Perkell, 1996, using his model presented in Perkell (1974);

Kiritani et al., 1976, Dang and Honda, 2004; Hashimoto and Suga, 1986; Payan and Perrier, 1997; Sanguineti et al., 1998; For 3D models, see Buchaillard, S., Perrier, P., Payan, Y., 2009; Wilhelms-Tricarico, 1995; Kakita et al., 1985)

The tongue implant should not limit movements in absolute terms like hyoid or tongue suspension for the treatment of OSA do, nor should it negatively influence speaking, mastication or swallowing. Out of these three tasks, not to influence speaking is the most difficult to cope with when placing an artificial member directly into the tongue. The production of speech involves complex muscles patterns. Some of these patterns are very fast, e.g. from a vowel to [k] about 30 ms, but doesn't involve strong muscle activation. Levels of forces generated by real speakers produced by the main muscles are in between 0.5 and 1.5 N. It must be noted, that these values measured are the force resultant. Inside the tongue accumulated forces are higher due to hydrostatic function of the tongue (Buchaillard and Perrier 2009). Since the production of speech is the fastest task with the lowest force production resultant, any device put directly into the tongue may create too much rigidity making it harder for the tongue to deform.

Other muscles activities, mainly mastication and swallowing, are deformations with stronger muscle activation. If the device makes swallowing or mastication movements harder in terms of necessary deformation forces, the increase would not be noted as easily or felt discomforting, because of stronger and slower muscle activation than in the production of speech. Regarding force levels, force distribution and deformations, these findings are essential to develop an implant to be placed directly inside the muscles of the tongue. The device must neither restrict movements of the tongue nor make speaking noticeably harder.

To simplify the complexity of the deformation analysis as well as to enhance the visual understanding, the 2D tongue deformation model of Perrier et al. (2003) has been chosen representing tongue characteristics that are relevant for speech and not the latest 3D models. Limiting the tongue model to the midsagittal plane is an acceptable simplification. In 2002 Badin et al. stated that <<most 3D geometry of tongue, lips and face can be—at least for speech—predicted from their midsagittal contours.>>It was verified in 2006 as Badin and Serrurier teach that "The error made in the prediction of the 3D tongue shapes from their midsagittal contours can finally be quantified by the difference between the overall full 3D RMS errors for the model (0.22 cm) and for the inversion based on the midsagittal error (0.25 cm): the mere 0.03 cm (13.6%) increase of this error testifies to the very good predictability of the 3D tongue surface mesh from its 2D midsagittal contour."

Accounting for tissue incompressibility would require measuring tissue deformations in 3D space, which obviously can't be done in a planar model. For that reason, tongue deformations in the direction orthogonal to the midsagittal plane were assumed to be negligible in comparison to the geometrical changes in this plane (plane strain hypothesis). Tissue quasi-incompressibility of the tongue is equivalent to area conservation and can be modeled with a Poisson's ratio value close to 0.5. This hypothesis is well supported by 3D measurements of tongue deformation during speech production, such as the ultrasound data published by Stone et al. (1997) or the MRI data analyzed by Badin et al. (2002). It can therefore be assumed, that for better understanding of midsagittal deformations during speech production, the model is fairly accurate and can serve as a basic model to address the underlying problem and solution. It is important to analyze extreme deformation patterns occurring inside the tongue in order to understand how and why it is crucial to insert a member helically from the root of the tongue, along and near the base of the tongue into the body of the tongue.

The intrinsic muscles as well as some extrinsic muscles contribute to a lesser extent to the sagittal tongue shape than the three major extrinsic muscles: the genioglossus, the styloglossus, and the hyoglossus, which are responsible for the main displacement and shaping of the overall tongue structure (Perkell, 1996). This has been reconfirmed in Perrier et al. 2003 and Buchaillard/Perrier 2009. The deformations produced by the three main muscles are by far the most extreme prototypical deformations patterns. Since deformations produced in speech are always activations of several muscles, the deformations never reach the extreme of these muscles activated solely. But if a helical pathway can fit into these extremes, deformation patterns of styloglossus, hyoglossus, posterior genioglossus and the tongue in rest position can be analyzed and with that the deformations between these extremes should be covered as well.

The problem with inserting a flexible, but in its longitudinal direction unelongatable member into the tongue in a straight or curved way is that the length of the pathway changes with the deformations of the tongue and that change could lead to a displacement and/or will definitely cause abrasion of the member due to relative movement between member and muscle fibers. To keep the member in place, a pathway which doesn't change its length needs to be found, which will also minimize relative movement. A well-adapted helical pathway, submentally pierced near the root of the tongue, along and near the base of the tongue into the body of the tongue can fulfill that criterion. The pierced helical pathway must have nearly equal length in all the extreme deformations of the tongue.

Figure 2:
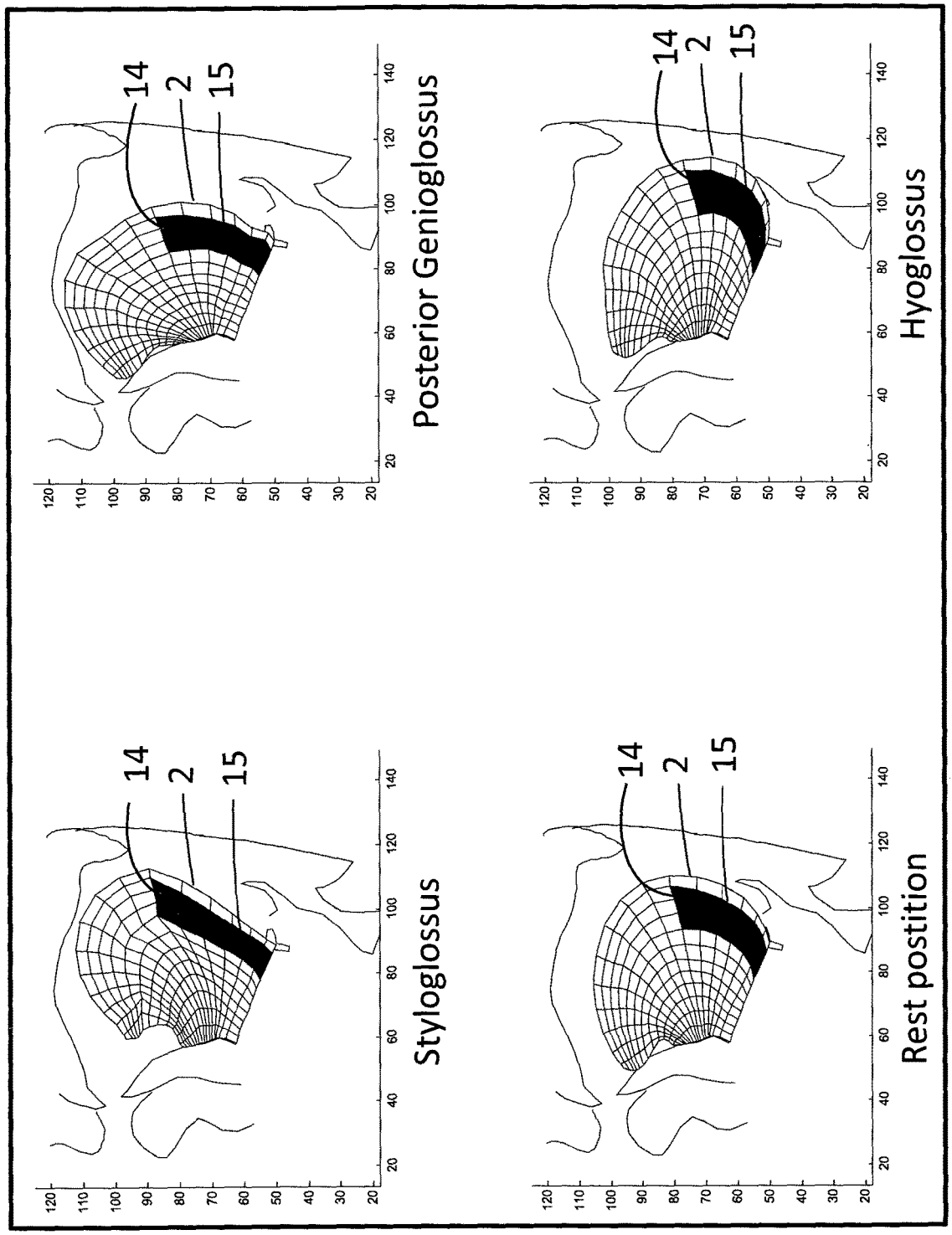
FIG. 2 is a midsagittal plane view of the pharynx of the Perrier (2003) tongue model showing a preferred site for tongue implantation and associated deformations of that section induced by the three main muscles and rest position.

Now referring to FIG. 2 tongue deformations induced by each modeled main extrinsic muscle are plotted with the tongue model of Perrier (2003). Direction and amplitude of the simulated deformations were verified to be compatible with data measured (Badin et al., 1995) The tongue shapes 2 shown in the figure are similar to those seen in a number of cineradiographic studies of speech movements (e.g., Perkell, 1969, Bothorel et al., 1986, Napadov, 1999 and 2002). The darkened section changes in length 13, width 14 and curvature as muscle are being activated. By piercing an helical pathway into that section and putting an implant inside, said implant can also change length and width, because it can substitute an increase in pitch with a decrease in diameter and vice versa. If the right pathway orientation and helical specifications are adequately defined, it could therefore deform and behave like the tongue with minimal relative movement between implant and tongue.

Figure 3:
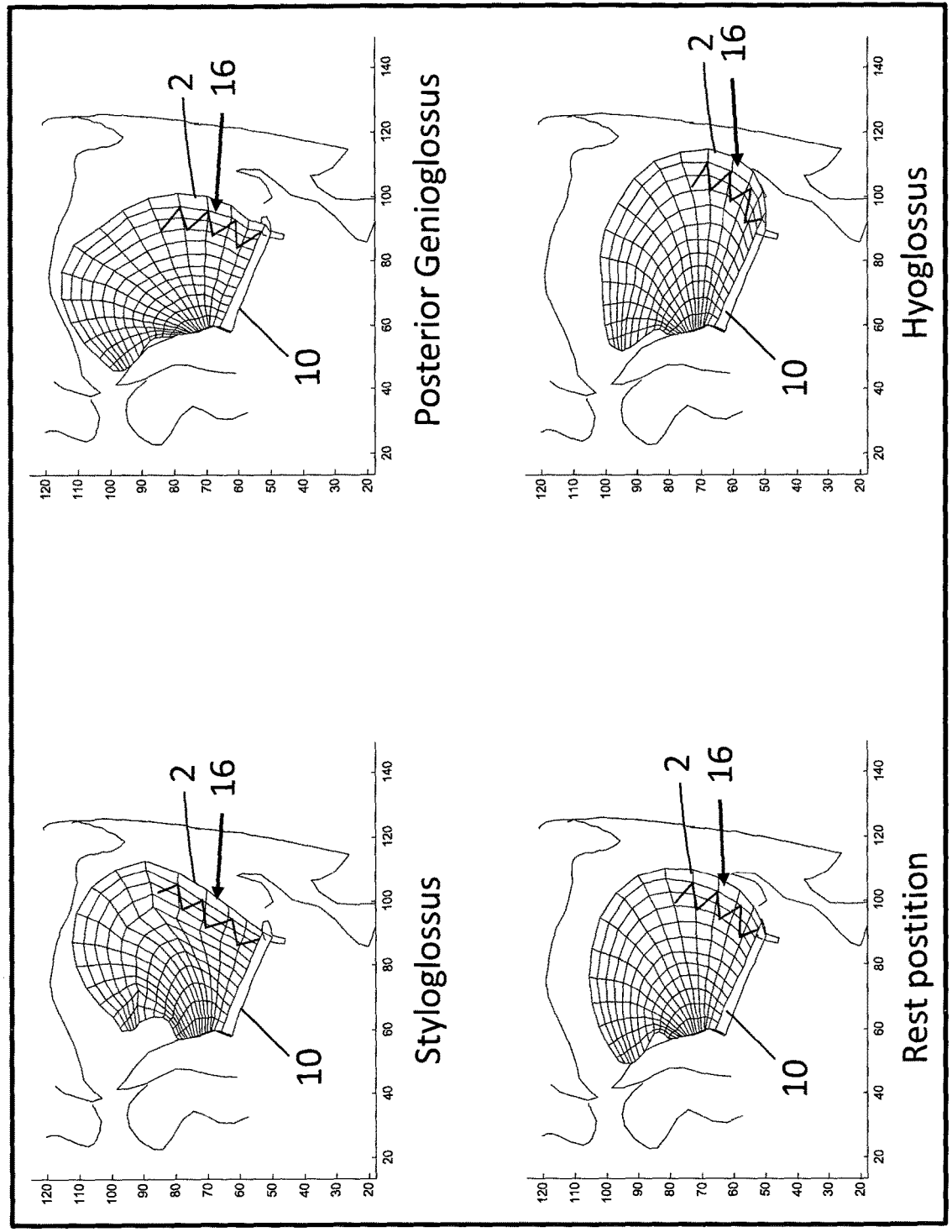
FIG. 3 is a midsagittal plane view of the pharynx of the Perrier (2003) tongue model showing a helical pathway and associated deformations of that section induced by the three main muscles and the rest position.

To achieve this, submental helical piercing is performed with the tongue in deformed state, like the deformation produced by styloglossus activation. As explained in International Patent Application PCT/IB2011/002878 entitled Helical Inserter, a Miller laryngoscope is put into the oral cavity down the pharynx to level of the epiglottis and the tongue is slightly pulled anteriorly (not shown in drawings), such that the base of the tongue is straightened before piercing the tongue helically. Such a pathway for the helical section 16 is shown in FIG. 3 for the deformation induced by the three main extrinsic muscles and the rest position. For simplicity of measuring length, a zigzag line is chosen to represent the helix, as it is a reasonable approximation in 2D.

Figure 4:
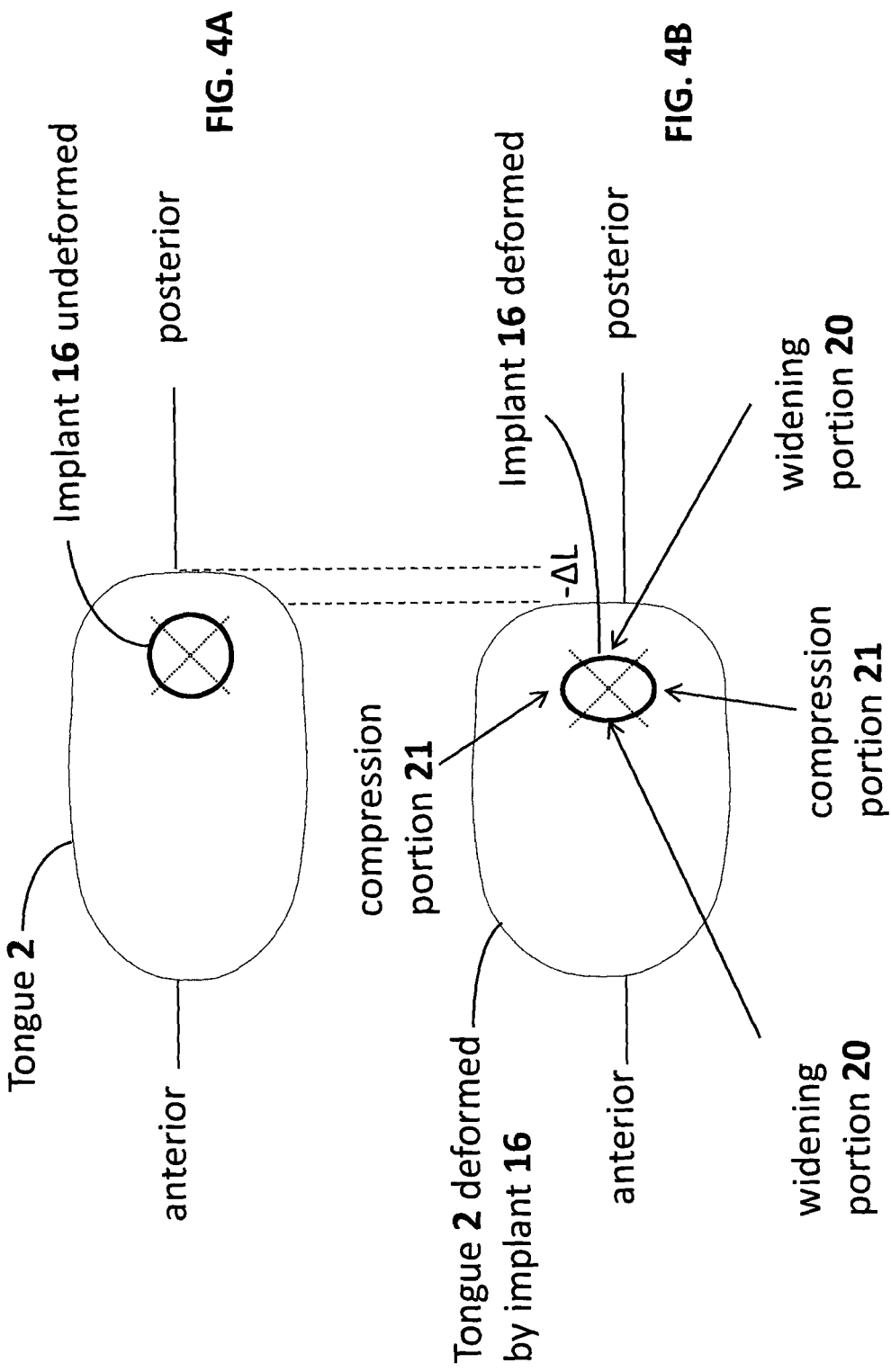
FIG. 4A is a top view on the tongue showing a helical implant inside the tongue in undeformed state when inserting it.
FIG. 4B is a top view on the tongue showing the deformation of a helical implant inside the tongue with associated change in length of the tongue.

Now referring to FIGS. 4 A&B, the helical section inside the body of the tongue 2 has four different portions: two widening portions 20 anteriorly and posteriorly and two compressing portions 21 creating an oval shape of the helix in top view, which deforms the tongue in a protruding way, as indicated with −ΔL in FIG. 4B. It must be explicitly noted that the helical section is not acting like a spring, which always pulls in direction of the axis when being expanded, as for example that disclosed in U.S. Pat. No. 8,220,466, the content of which is incorporated by reference thereto. The helical section in this implant compresses the tissue towards the axis of the helix in midsagittal plane and it is inserted through helical piercing with the axis in close to parallel orientation to the spine in midsagittal plane view.

Figure 5:
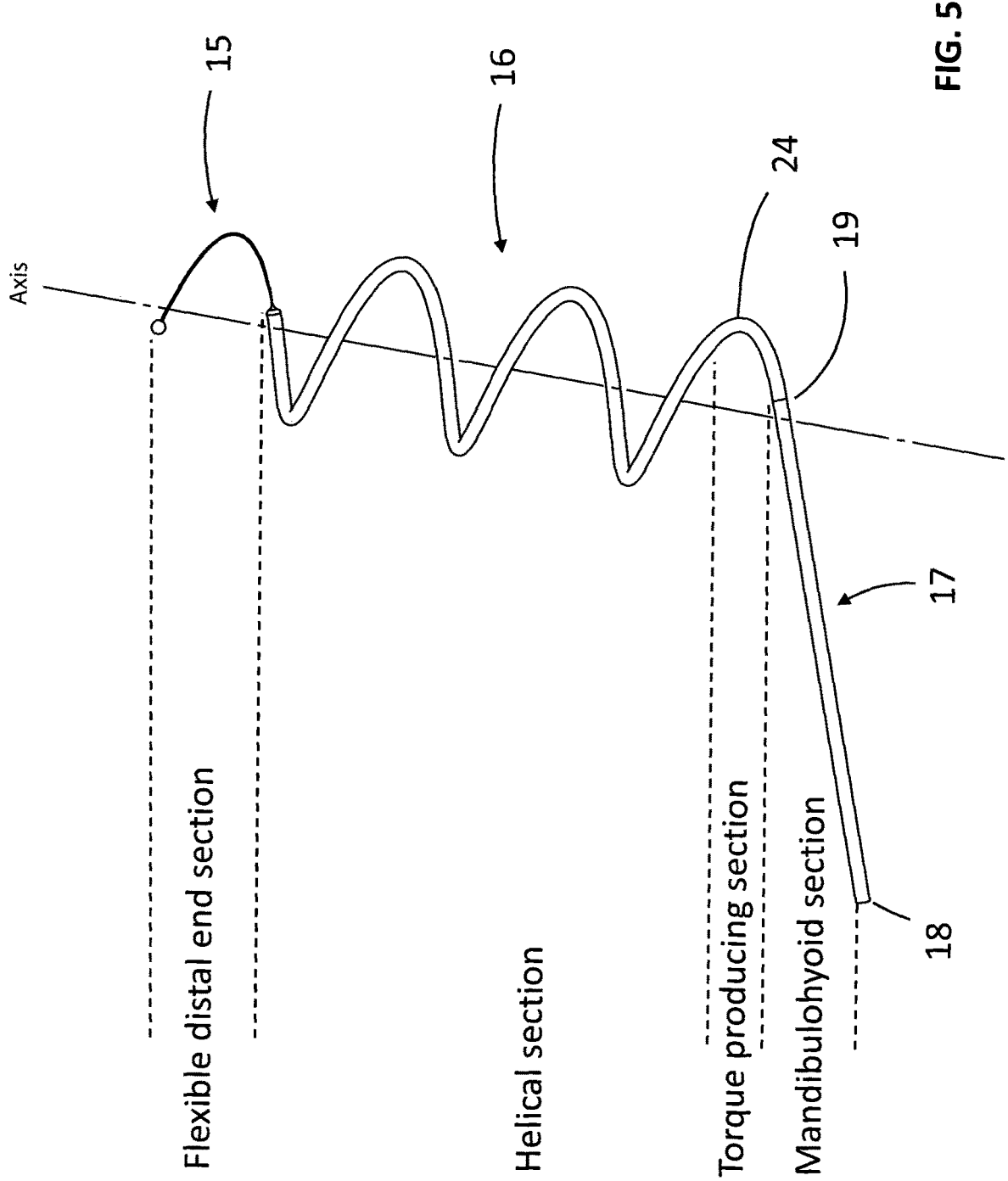
FIG. 5 is a front view of a tongue implant showing all sections.
Figure 6:
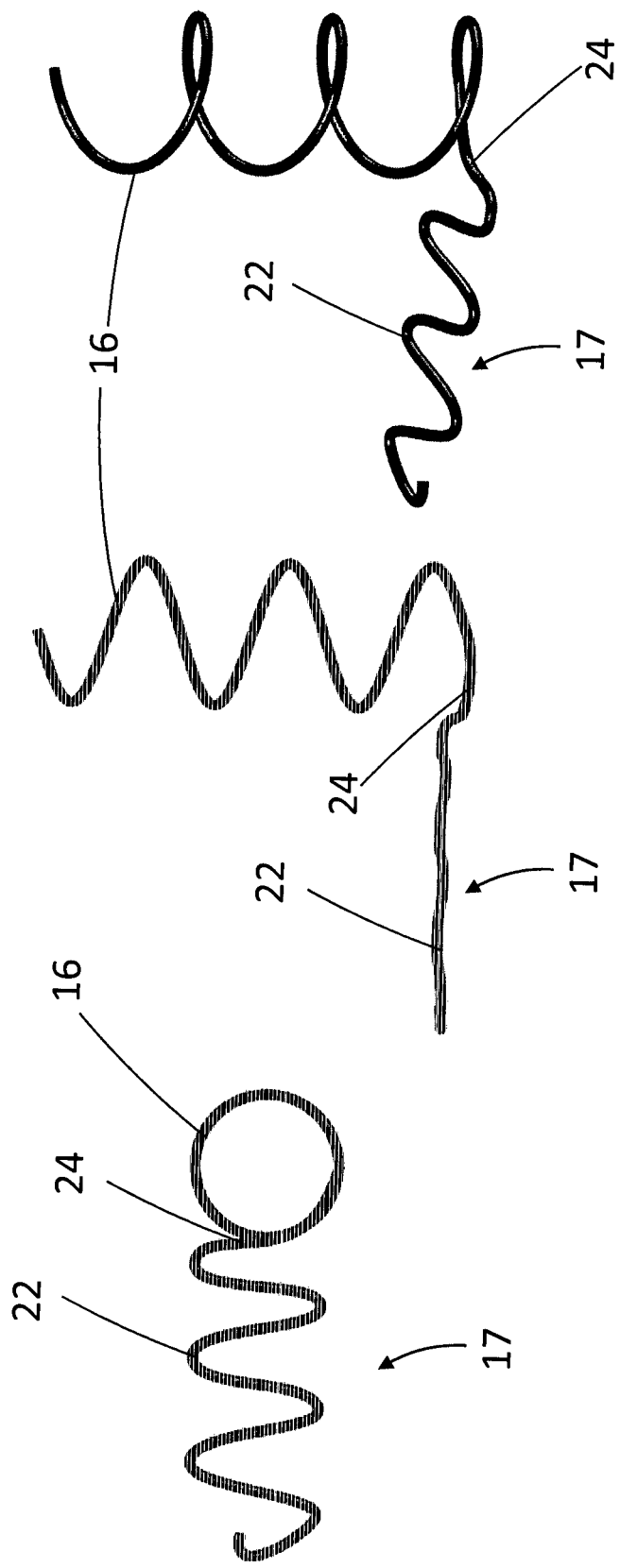
FIG. 6A shows a bottom view of the implant with the mandibulohyoid section for force distribution shaped in serpentine way without the flexible distal end section.
FIG. 6B shows a side view of the implant with the mandibulohyoid section for force distribution shaped in serpentine way without the flexible distal end section.
FIG. 6C shows a perspective view of the implant with the mandibulohyoid section for force distribution shaped in serpentine way without the flexible distal end section.
Figure 7:
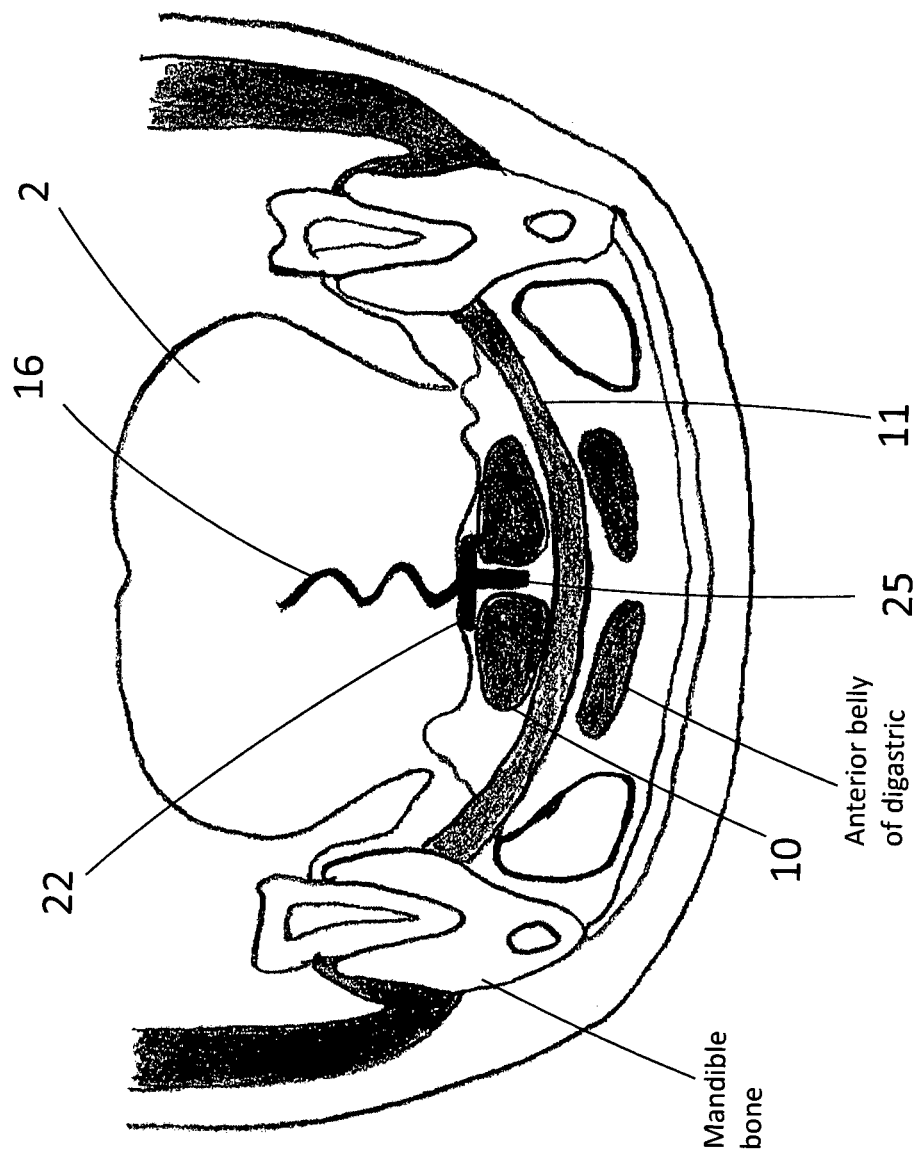
FIG. 7 is a coronal plane cross section of the mandible showing placement of the mandibulohyoid section including a fin.
Figure 14:
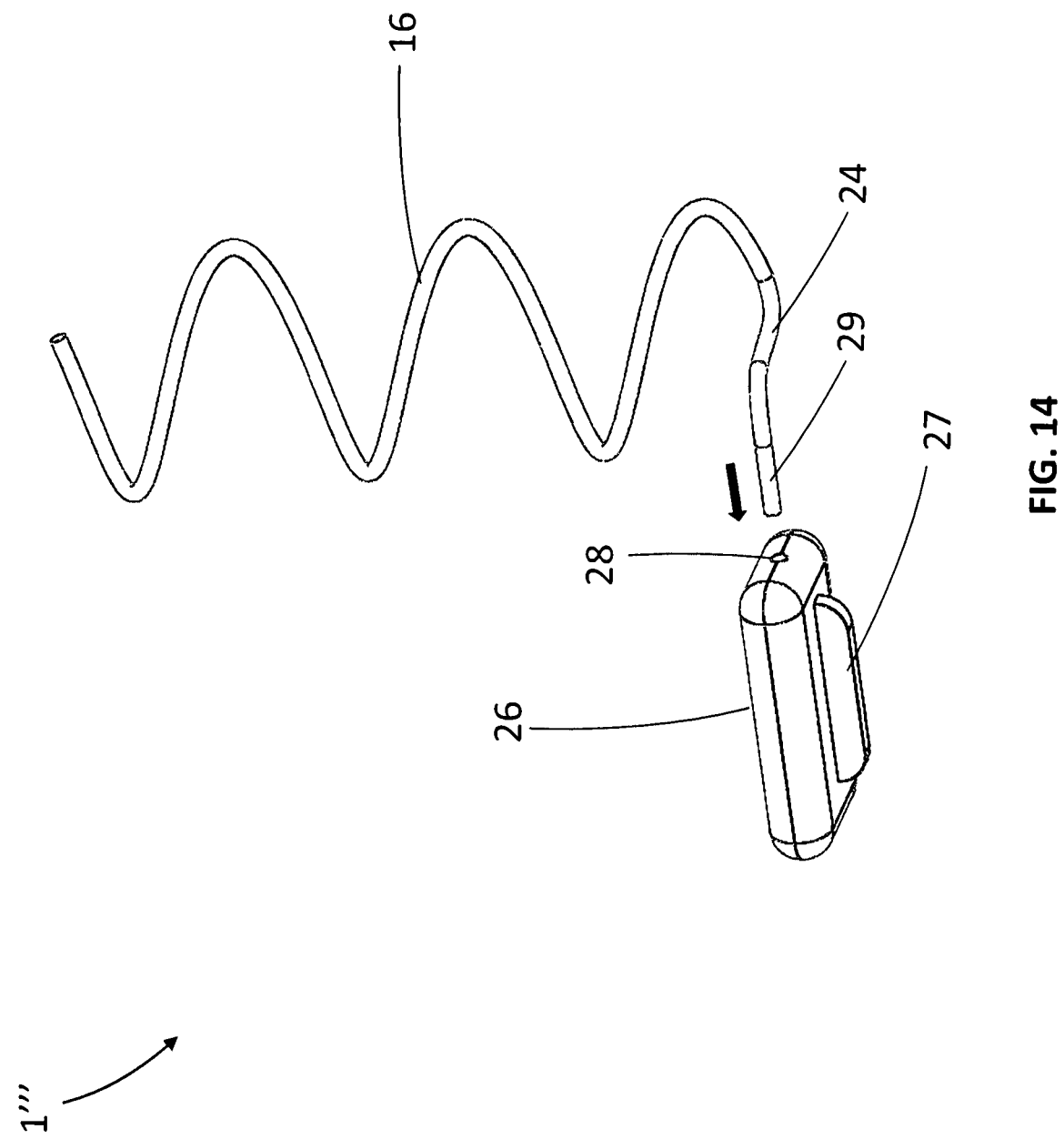
FIG. 14 is another embodiment for a force distributing mandibulohyoid section without the flexible distal end section.

Now referring to FIG. 5, which describes the basic V spring setup, one embodiment comprises four sections: the flexible distal end section 15, the helical section 16 inside the body of the tongue 2, the torque providing section 24 at entry of the root of tongue, and the mandibulohyoid section 17 for force distribution. The flexible distal end section 15 provides means for stabilization of the member distally inside the body of the tongue allowing small displacement of the helical section 16 to avoid poking of the tissue as the tongue is performing its physiological tasks, which might be noted as tingling sensation. The helical section 16 providing means to exert a force on the tongue towards the axis of the helix, essentially stiffening and compressing it along the base of the tongue and protruding the tongue. The mandibulohyoid section 17 providing means for force distribution of the torque produced 24. Now referring to FIG. 6, there is provided a force distribution section placed between geniohyoid 10 and root of tongue having a shape of a serpentine line 22 to better distribute the force produced by the torque section 24 and compress the body of the tongue stiffening and protruding it. Now referring to FIG. 7, to prevent dislocation laterally of the mandibulohyoid section, a fin 25 can be shaped for placement without attachment between the two geniohyoid muscles 10. Now referring to FIG. 14, explaining another embodiment of the mandibulohyoid section 1''', instead of creating a shape like a serpentine line for force distribution of the torque producing section 24, a force distributing part 26 could be placed between geniohyoid 10 and body of tongue or between mylohyoid 11 and geniohyoid 10, preferably made of a polymer. This part would be slipped into the target site and then attached to the member as indicated by the arrow, for example by an aperture 28 with a corresponding distal end 29 of the member. Again, to prevent dislocation laterally, a fin 27 is added to be placed between the two geniohyoid muscles 10.

In another embodiment, only the helical section and the flexible distal end section are used, thus only compressing the tongue along the base of the tongue, the implant not acting like a V shaped spring.

Superelastic Nickel-Titanium (nickel titanium alloy or NiTi) has become the material of choice for self-expanding, stents, stent grafts, filter, baskets and other devices for interventional procedures. With the demand for high precision NiTi material in different forms, especially wire and tubes, immense progress has been made in the manufacturing processes, making it possible to get material in a wide range of geometries and sizes.

What makes nickel titanium alloy unique is its ability to exist in two different temperature-dependent crystal structures (phases) called martensite (lower temperature) and austenite (higher temperature); superelasitc nickel titanium alloy is fully in austenite state.

While most metals can be deformed by slip or dislocation, NiTi responds to stress by simply changing the orientation of its crystal structure through the movement of twin boundaries. A NiTi specimen will deform until it consists only of the correspondence variant, which produces maximum strain. However, deformation beyond this will result in classical plastic deformation by slip, which is irrecoverable and therefore has no 'memory effect'. If the deformation is halted midway, the specimen will contain several different correspondence variants. If such a specimen is heated above Af, a parent phase with an orientation identical to that existing prior to the deformation is created from the correspondence variants in accordance with the lattice correspondences between the original parent phase and each variant.

The austenite crystal structure is a simple cubic structure, while martensite has a more complex rhombic structure. This phenomenon causes the specimen to revert completely to the shape had before the deformation. The above phenomenon is the basis of such special properties as the shape memory effect and superelasticity. The properties of nickel titanium alloy rely on this dynamic crystalline structure. The molecular structure is sensitive to external stress and temperature. The alloy has three defined temperature phases.

1. Austenite Phase (Superelastic State).

Temperature is above transition temperature. The transition temperature varies depending upon the exact composition of the nickel titanium alloy; today it can be fine-tuned to a specific temperature. The yield strength with which the material tries to return to its original shape is considerable; 35,000 to 70,000 psi. The Crystalline structure is cubic.

2. Martensitic Phase.

Low temperature phase. The crystal structure is needle-like and collected in small domains. Within the small domains the needle-like crystals are aligned. The alloy may be bent or formed easily and will remain in that shape. Deformation pressure is 10,000 to 20,000 psi. Bending transforms the crystalline structure of the alloy producing an internal stress.

3. Annealing Phase.

High temperature phase. The alloy will reorient its (cubic) crystalline structure to "remember" its present shape. The annealing phase for the nickel titanium alloy wire is about 540° C. A CNC torsion spring coiler machine like the FMU series of German producer Wafios could be used to produce a tube, for example a stainless steel tube, having the desired shape which the nickel titanium alloy should have. The nickel titanium alloy tube or wire will be pulled into the formed tube for annealing.

Due to the high cyclic deformation load the implant is subjected to as the tongue performs its physiological task, the strain should be kept low, at best below 0.5% to avoid early fatigue of the nickel titanium alloy to enhance longevity. This can be influenced by choosing the helical pathway pierced through the tongue well. The pierced pathway should have a diameter between 4 mm to 30 mm with a pitch between 3 mm to 20 mm. The orientation of piercing in midsagittal plane should be almost parallel to the spine. The common mechanical properties of austenitic NiTi are presented in Table 1.

Table 1
Selected mechanical properties of NiTi Austenite
Ultimate tensile strength (MPa) 800-1500

TABLE 1

| Selected mechanical properties of NiTi | Austenite |
| --- | --- |
| Tensile yield strength(MPa) | 100-800 |
| Modulus of elasticity (GPa) | 70-110 |
| Elongation at failure (%) | 1-20 |

It is feasible to vary the critical transition temperatures either by small variations of the Ti/Ni composition or by substituting metallic cobalt for nickel.

Referring to FIG. 8, a tube having a constant diameter could be used, but this might create too much rigidity towards the distal end inside the tongue body. Another basic shape would be cone like because the most force for deformation of the tongue is need at the root of the tongue and less force is required towards the flexible distal end of the member inside the tongue body. However, since it isn't necessary to have the same amount of force exerted along the whole length of the member, the nickel titanium alloy tube or wire can be grinded, laser cut or structured laser ablated to a profile such that with every half turn it is thinner (the widening portion 20) than the compressing portion 21 in between. The smaller profile 20 is used so that the tongue can deform at these sections, the member only requiring minimal deformation forces when the tongue is performing its physiological tasks during daytime. The thicker sections are needed to deform the tongue at night when OSA occurs with muscles inactive. Since the force that the member can exert on the tongue is directly dependent on its square area, this is the section which is deforming and changing the stiffness of the tongue. The compression portion of the helix facing posteriorly (towards the pharynx) must be stronger than the ones facing anteriorly (towards the front teeth). This creates segments between each pitch and deforms the tongue in a protruding way. Pressure exerted should be between 2 kPa and 25 kPa. The diameter of the nickel titanium alloy wire should be between 50 µm to 700 µm or for a tube, the ID about 600 µm and OD about 1.2 mm.

Figures 10A, 10B:
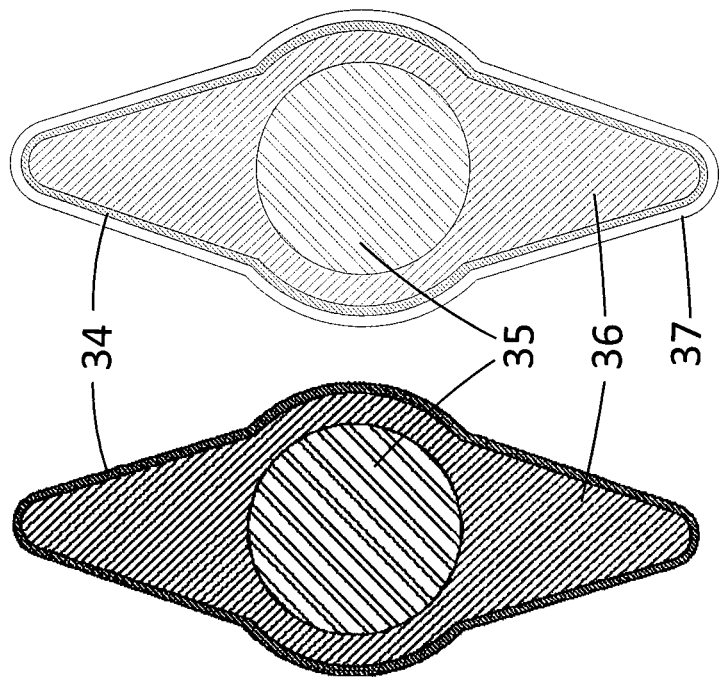
FIG. 10A shows a cross section of the helical section a nickel titanium alloy wire embedded in silicone rubber and having a fluoropolymer coating.
FIG. 10B shows a cross section of the helical section a nickel titanium alloy wire embedded in silicone rubber having a fluoropolymer coating and an outer hull of a UHMWPE fabric.
Figure 9:
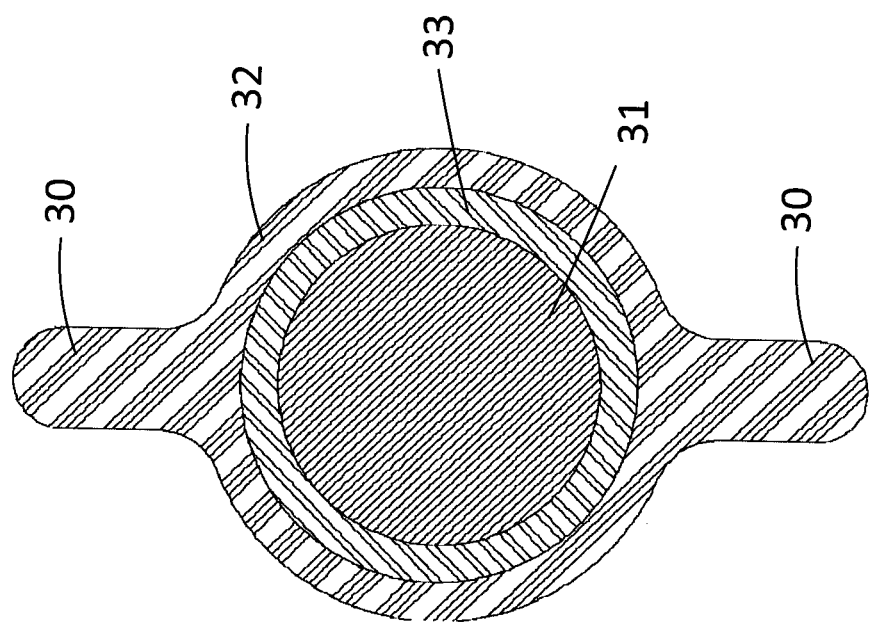
FIG. 9 shows a cross section of the helical section of a nickel titanium alloy tube.

Now referring to FIGS. 9 and 10A&B, showing three cross sections of the helical section 16, the problem with putting a force exerting nickel titanium alloy implant into soft tissue like muscles of the tongue is that the modulus of elasticity of nickel titanium alloy in superelastic state is very high (70-110 GPa) and the modulus of elasticity of muscles is low (a few kPa) creating a great mismatch between these two materials. The nickel titanium alloy might therefore "cut" through soft tissue as observed in with the Repose System to treat apnea. To avoid this behavior, the modulus of elasticity of the nickel titanium alloy implant device may be lowered by increasing the surface area where the force is exerted and combining it with a material having a low modulus of elasticity.

To increase the surface area, wings 30 are added to the device oriented perpendicular to the force exerted, which means the wings are in parallel orientation to the axis of the helix. Further the nickel titanium alloy is combined with silicone rubber or the like having a low modulus of elasticity.

Now referring to FIG. 9, a nickel titanium alloy tube 33 with a silicone rubber core 31 and an outer hull a fluoropolymer 32 having wings 30 is produced by following the steps of:

1. Producing a stainless steel tube having the desired shape the nickel titanium alloy should have with an ID slightly larger than the OD of the nickel titanium alloy tube;
2. Pulling the nickel titanium alloy tube inside the stainless steel tube;
3. Annealing;
4. Pulling nickel titanium alloy out of stainless steel tube;
5. Closing one end of the nickel titanium alloy tube by putting a short nickel titanium alloy wire (0.5 mm length) into the distal end of the tube and laser weld both parts together;
6. Cooling the nickel titanium alloy tube down to its martensite phase;
7. Pulling the nickel titanium alloy tube inside a straight stainless steel tube having a slightly larger ID than the OD of the nickel titanium alloy tube;
8. Increasing the ID of the nickel titanium alloy tube by pressurizing it with air or water inside the stainless steel tube (the increased diameter will remain as long as the nickel titanium alloy tube is in martensite);
9. Cutting of the closed distal end of the nickel titanium alloy tube;
10. Pulling a prefabricated silicone wire having an OD corresponding to the original ID of the nickel titanium alloy tube inside;
11. Heating the nickel titanium alloy tube up to change the phase to austenite which will cause the nickel titanium alloy to shrink to its original size creating form fit between the two materials;
12. Cooling the nickel titanium alloy down to martensite and straighten it without twisting;
13. Placing the nickel titanium alloy tube to the infeed of a ram extrusion machine to create the fluoropolymer outer hull having wings, push or draw through a die of the desired cross-section;
14. Thermal curing the fluoropolymer; and
15. Cutting of residual material on both ends;

In case of using silicone instead of silicone rubber for the core 31, the silicone is filled inside the nickel titanium alloy tube 33, and the end of the tube is closed with a short nickel titanium alloy wire (0.5 mm) having an OD corresponding the ID, then laser weld the two parts together.

Now referring to FIGS. 10A&B, a nickel titanium alloy wire 35 is embedded in silicone rubber 36 of the desired cross section and later coated with a melt processable fluoropolymer 34 by following the steps of:

1. Producing a stainless steel tube having the desired shape the nickel titanium alloy should have with an ID slightly larger than the OD of the nickel titanium alloy wire;
2. Pulling the nickel titanium alloy wire inside the stainless steel tube;
3. Annealing;
4. Pulling nickel titanium alloy out of stainless steel tube;
5. Cooling the nickel titanium alloy down to martensite and straighten it without twisting;
6. Placing the nickel titanium alloy wire to the infeed of a ram extrusion machine to create the silicone rubber outer hull, push or draw through a die of the desired cross-section;
7. Vulcanizing;
8. Cutting of residual material on both ends;

The above-stated materials of making the nickel titanium alloy tube 33 and nickel titanium alloy wire 35 are part of the invention and are intended to be claimed as such in a later filed divisional application.

Now referring to FIG. 10B, to further protect the fluoropolymer coating 34 from wear inside the tongue due to small relative movements, a woven or braided fabric 37 surface can be created with a ultra-high-molecular-weight polyethylene (UHMWPE) fiber, for example like Dyneema of Royal DSM N.V., having the advantage of very high wear resistance. Since the UHMWPE can't be joined with the fluoropolymer, only the tension created of the woven fabric holds it in place. Therefore, wings cannot be formed because it would create a void, but instead, an equilateral triangle can be formed on both sides of the wire.

For both production techniques described, the nickel titanium alloy tube or wire must be aligned before placing it to the infeed of the ram extrusion, so that the wings or increased surface area is in the desired orientation before pushing it through the die of the ram extrusion. This could be achieved by laser marking the nickel titanium alloy tube or wire. For example, the stainless steel tube needed for shape setting of the nickel titanium alloy could have several small drill holes at predetermined places so that the laser marking can be done after annealing, before the nickel titanium alloy is pulled out the stainless steel tube. These markings are later used to keep the orientation when placing the nickel titanium alloy into the infeed of the ram extrusion.

Figure 12A:
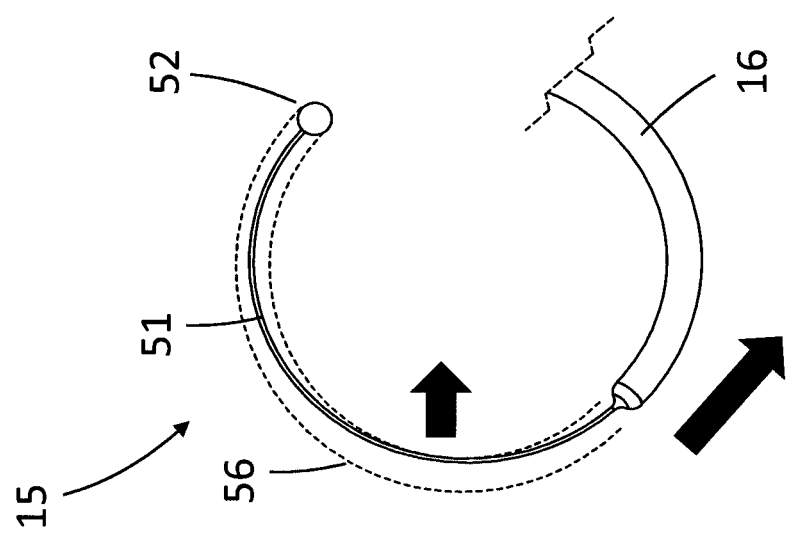
FIGS. 12A&B shows the distal end section reacting to a small dislocation of the distal end of the helical section inside the tissue.
Figure 12B:
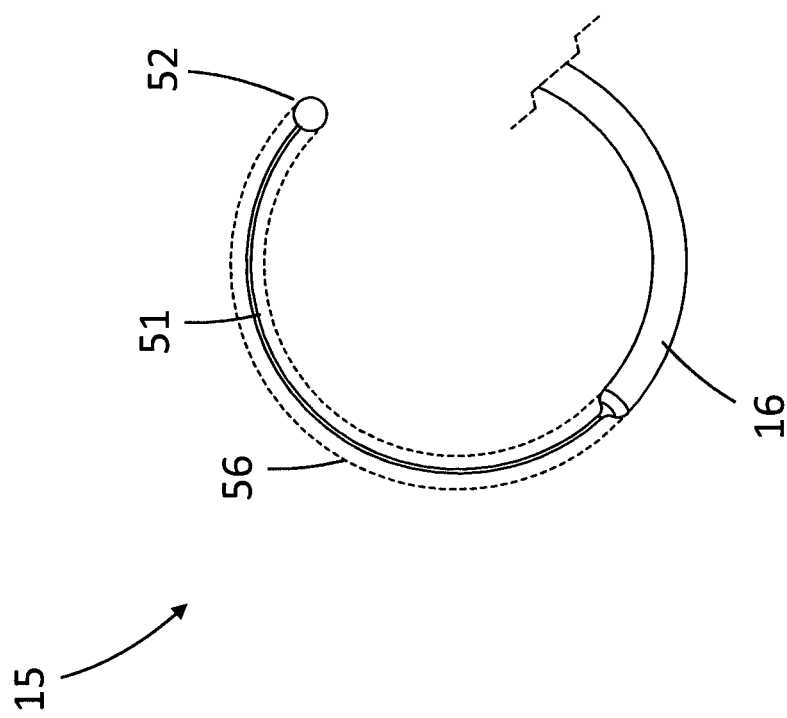

Now referring to FIGS. 11-13, the flexible distal end section 15 must be designed that the member can neither be displaced nor can it poke tongue tissue. But it must leave the option of extraction of the implant without cutting the whole tongue open, but rather just by pulling it out of the body of the tongue. A polymeric fiber 51, for example a polyamide, substantially smaller in diameter, for example 30 µm, is attached at the flexible distal end 44 of the helical section 16. At the distal end 52 of the distal end section 15, a sphere could be attached to the fiber 51 having the same diameter as the helical section 16, but it could have other shapes. The pressure inside the tongue tissue 56 will hold in place. Another option shown in FIG. 13 would be to shape the distal end 44 of the helical section 16 like a cone and to shape the distal end of 15 like a cone 54 as well, but facing reverse direction. This allows for small displacement, but the cone shape will make it slide back to an initial position. This could be further enhanced by shaping the distal end of the distal end section 53 in concave form. The distal end section and the helical section can be joined together for example by means of laser welding 55 or pressfitting it to the nickel titanium alloy.

In an advantage, a tongue implant for the treatment of OSA is provided which is easy to install in a minimally invasive manner.

In another advantage, a tongue implant is provided which can deform the tongue to comply with physiological tasks, but changes its rigidity to reliably and safely open up the pharyngeal airway blocked by the tongue.

In another advantage, the implant stiffens the tongue along its base into the body of the tongue and protrudes it.

In another advantage, the implant once installed, minimizes relative movement between itself and the surface area of the tongue in contact with it, to minimize abrasion.

In an advantage, the implant and method of the invention allow for the use of a nickel titanium alloy material while having a lower overall modulus of elasticity, to protect the tongue.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

The copyrights are owned by the Applicant(s) or their assignee and, with respect to express Licensees of the rights defined in one or more claims herein, no implied license is granted herein to use the invention as defined in the remaining claims. Further, vis-à-vis third parties, including the public, no express or implied license is granted to reproduce, prepare derivative works, distribute copies, display, or otherwise use this patent specification, inclusive of the appendix hereto and any computer program comprised therein, except as an appendix to a patent issuing hereon.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the claims which ultimately issue in this application.

In an embodiment, an implant for treating obstructive airway disorders comprises an element forming a helix in a helical section of the implant adapted such that the implant is helically insertable along the base of the tongue along a helically pierced pathway such that, when implanted, the implant compresses the tongue by producing a force directed toward an axis of the helix.

In an embodiment, the element is adapted such that the force deforms the helical pathway to an oval shape in a plane transverse to the helical pathway.

In an embodiment, the oval shape has a larger diameter directed along the coronal plane of the tongue.

In an embodiment, the element in the helical section comprises compression portions and widening portions for producing the force towards the axis of the helix.

In an embodiment, the cross section of the widening portions is smaller than a cross section of the compression portions.

In an embodiment, the compression portions and widening portions alternate every quarter turn of the helical section.

In an embodiment, the element in the helical section is shaped as a cone such that an end of the element to be inserted first has a smaller cross section than an opposite end of the element.

In an embodiment, the element in the helical section is shaped as a profiled cone with alternate fibered parts having larger and smaller cross-sections.

In an embodiment, the element comprises NiTi adapted to be in superelastic state at body temperature.

In an embodiment, the element comprises a NiTi wire having an elastomeric outer hull.

In an embodiment, the elastomeric outer hull is made of silicon rubber.

In an embodiment, the silicone rubber is formed to increase the surface area perpendicular of the force exerted to decrease the pressure at a given force on soft tissue.

In an embodiment, the silicone rubber is protected with a fluoropolymer coating.

In an embodiment, the silicone rubber is protected with a woven or braided fabric of a UHMWPE fiber.

In an embodiment, the fluoropolymer coating is protected with a woven or braided fabric of a UHMWPE fiber.

In an embodiment, comprising a woven or braided fabric surface surrounding the outer hull, preferably created with UHMWPE fiber.

In an embodiment, the element comprises a NiTi tube filled with a silicon or silicon rubber core and having a fluorpolymer outer hull.

In an embodiment, the outer hull has wings.

In an embodiment, the implant further comprises a flexible distal end positioned adjacent the helical section.

In an embodiment, the implant further comprises a torque-producing section and a force distributing section, wherein the torque producing section and force distributing section are adapted such that when implemented into a patient's tongue the implant biases the tongue to return toward a second deformed shape without requiring tissue attachment.

In an embodiment, the torque-producing section is positioned between the force distributing section and the helical section and opposite the flexible distal end.

In an embodiment, the force distributing section is adapted for placement between the root of the tongue and the geniohyoid muscle.

In an embodiment, the force distributing section is adapted for placement between the geniohyoid and the mylohyoid muscle.

In an embodiment, a fin is formed to be placed between the two geniohyoid to prevent dislocation.

In an embodiment, the force distributing sections are attached to hyoid bone.

In an embodiment, the force distributing section are attached to the mandible bone exerting a pulling force.

In an embodiment, the force distributing section further comprises an axially compliant FIN adapted to be placed between the two geniohyoid muscles thereby preventing dislocation.

In an embodiment, wherein the element comprises a NiTi tube.

In an embodiment, the NiTi tube is filled with a fluid.

In an embodiment, the NiTi tube is filled with oil.

In an embodiment, the NiTi tube is filled with an elastomer.

In an embodiment, the forces exerted vary along the implant member ranging between 0 and 25 kPa, variable through a defined variation in diameter of the implant.

In an embodiment, the coating is an elastomer.

In an embodiment, the flexible distal end is made of a flexible polymer fiber.

In an embodiment, the distal end of the flexible distal end section has a substantially spherical shape.

In an embodiment, the distal end of the flexible distal end section has a substantially spherical shape.

In another aspect, the invention relates to a method for using an implant for treating obstructive airway disorders, the method comprising the steps of:

inserting an NiTi implant in superelastic state at body temperature, the implant having a deformable helix, a flexible distal end, a torque-producing section and a force distributing section; and placing one end of the implant helically in a patient's tongue to bias the implant to return the tongue toward a second deformed shape after inserting and therewith compressing and stiffening the tongue to preferred shape without requiring tissue attachment, the torque producing section leaving the root of the tongue and the force distributing section, connected thereto at an apex, being placed outside the tongue body.

In another aspect, the invention relates to a method for using an implant for treating obstructive airway disorders, the method comprising:

providing a NiTi device in superelastic state at body temperature; and piercing a helical pathway in the tongue and implanting the NiTi device in superelastic state at body temperature helically along the base of the tongue essentially parallel to the spine on the midsagittal plane, so that the implant compresses the tongue by producing a force directed toward the axis of the helically pierced pathway deforming the helical pathway to an oval shape on the transverse plane, the larger diameter of oval directed along coronal plane.

In an embodiment, the pierced helical pathway for the implant has a diameter between 3 mm and 22 mm.

In an embodiment, the pitch of the pierced helical pathway for the implant is between 3 mm and 25 mm.

In an embodiment, the orientation of the axis of the pierced pathway in comparison to the spine in midsagittal plane is between +50 degrees and −50 degrees.

In another aspect the invention relates to a method for using an implant for treating obstructive airway disorders, the method comprising:

providing a NiTi device in superelastic state at body temperature; and permanently implanting the NiTi device in superelastic state at body temperature helically along the base of the tongue essentially to parallel to the spine on the midsagittal plane along a pathway that does not substantially change its length during articulation through extreme tongue movements.

What is claimed is:

1. An implant for treating obstructive airway disorders comprising an element forming a helix having a helix axis in a helical section of the implant wherein, at body temperature, the helical section is elastic and exhibits an oval shape as seen along the helix axis, such that, when implanted along a helically pierced pathway in the tongue, the implant compresses the tongue by a force directed toward the helix axis.

2. The implant of claim 1, wherein the element is adapted such that the force deforms the helically pierced pathway to an oval shape in a plane transverse to the helically pierced pathway.

3. The implant of claim 2, wherein the oval shape of the helically pierced pathway has a larger diameter directed along the coronal plane of the tongue.

4. The implant of claim 1, wherein the element in the helical section comprises compression portions and widening portions for producing the force towards the axis of the helix.

5. The implant of claim 4, wherein a cross section of the widening portions is smaller than a cross section of the compression portions.

6. The implant of claim 4, wherein the compression portions and widening portions alternate every quarter turn of the helical section.

7. The implant of claim 1, wherein the element in the helical section is shaped as a cone such that an end of the element to be inserted first has a smaller cross section than an opposite end of the element.

8. The implant of claim 7, wherein the element in the helical section is shaped as a profiled cone with alternate fibered parts having larger and smaller cross-sections.

9. The implant of claim 1, wherein the element comprises NiTi adapted to be in a superelastic state at body temperature.

10. The implant of claim 9, wherein the element comprises a NiTi wire having an elastomeric outer hull comprising a silicone rubber.

11. The implant of claim 10, wherein the silicone rubber is formed to increase the surface area perpendicular to the force exerted, in order to decrease a pressure at a given force on soft tissue.

12. The implant of claim 10, wherein the silicone rubber is protected with at least one of a fluoropolymer coating and a woven or braided fabric of a UHMWPE fiber.

13. The implant of claim 10, wherein the outer hull has wings.

14. The implant of claim 1, wherein the implant further comprises a flexible distal end section positioned adjacent the helical section.

15. The implant of claim 1, wherein the implant further comprises a torque-producing section and a force distributing section, wherein the torque producing section and force distributing section are adapted such that when implemented into a patient's tongue the implant biases the tongue to return toward a second deformed shape without requiring tissue attachment.

16. The implant of claim 15, wherein the force distributing section is adapted for placement between the root of the tongue and the geniohyoid muscle, or is adapted for placement between the geniohyoid and the mylohyoid muscle.

17. The implant of claim 15, wherein the force distributing section is adapted to be attachable to the mandible bone for exerting a pulling force and/or is adapted to be attachable to the hyoid bone.

18. The implant of claim 15, wherein the force distributing section further comprises an axially compliant fin adapted to be placed between the two geniohyoid muscles thereby preventing dislocation.

19. The implant of claim 7, wherein the forces exerted vary along the implant member ranging between 0 and 25 kPa, variable through a defined variation in diameter of the implant.

20. The implant of claim 14, wherein the distal end of the flexible distal end section has a spherical shape or a conical shape.

* * * * *